(12) United States Patent
Sideris

(10) Patent No.: US 6,238,416 B1
(45) Date of Patent: May 29, 2001

(54) TRANSCATHETER SURGICAL PATCH

(76) Inventor: Eleftherios B. Sideris, Suite 200 1600 Coulter, Amarillo, TX (US) 79106

( * ) Notice: Subject to any disclaimer, the term of this patent is extended or adjusted under 35 U.S.C. 154(b) by 0 days.

(21) Appl. No.: 09/435,202

(22) Filed: Nov. 5, 1999

Related U.S. Application Data

(60) Provisional application No. 60/108,405, filed on Nov. 13, 1998.

(51) Int. Cl.$^7$ .................................................. A61B 17/08
(52) U.S. Cl. .......................................... 606/213; 128/897
(58) Field of Search ..................................... 606/151, 153, 606/213, 215; 600/37; 128/897–899, 887

(56) References Cited

U.S. PATENT DOCUMENTS

| | | | |
|---|---|---|---|
| 4,917,089 | 4/1990 | Sideris | 606/215 |
| 5,284,488 | 2/1994 | Sideris | 606/213 |
| 5,433,727 | 7/1995 | Sideris | 606/213 |
| 5,792,179 | 8/1998 | Sideris | 606/213 |

Primary Examiner—John P. Lacyk
(74) Attorney, Agent, or Firm—Wendell Coffee

(57) ABSTRACT

A heart defect in the form of an hole is corrected by placing a patch over the hole. The patch is first attached to an uninflated balloon which is placed distally of the hole. The balloon is inflated with fluid and the patch is positioned upon the hole. After endothelialization the balloon is deflated and removed through a small hole in the patch. The small hole in the patch is closed by a purse string. During endothelialization the balloon is held in place by a disk or second balloon on the proximate side of the defect.

6 Claims, 2 Drawing Sheets

TRANSCATHETER SURGICAL PATCH

CROSS REFERENCE TO RELATED APPLICATION

Applicant filed a Provisional Application on this subject matter on Nov. 13, 1998 Ser. No. 60/108,405. Specific reference is made to that document.

BACKGROUND OF THE INVENTION (1) Field of the Invention

This Invention relates to a transcatheter surgical patch placement for the correction for heart defects. This procedure will normally be applied to patients with heart defects.

(2) Description of the Related Art

Transcatheter heart defect repair is traditionally done by the use of double disk devices. A basic requirement for the use of the double disk devices is the presence of sufficient rim or healthy septal tissue around the defect; because of that the double disk devices are restricted to relatively small central defects. Furthermore, all devices utilize metal skeleton frame with various immediate serious wire related complications and unknown long term side effects for the human body.

The surgeons repair the heart defects utilizing patches of different materials which they suture onto the heart. Suturing is dangerous since it can traumatize the heart or the conduction system causing heart block. Furthermore, thoracotomy and open heart surgery is required for most cases.

SUMMARY OF THE INVENTION (1) Progressive Contribution to the Art

It is believed Transcatheter patch placement without suturing has not been described before.

A method for sutureless Transcatheter patch placement for the correction of heart defects is described herein. The importance and the potential of such a method is great, since minimal septal rim is required and the majority of heart defects can be repaired without cutting surgery, surgical sutures, or permanent device implantation.

In addition to defect repair, Transcatheter patch placement can find several other applications including but not limited to heart valves, internal vascular work and even coronary artery surgery. Furthermore, surgeons could use the sutureless technique is to avoid suture related injury during surgery.

The Transcatheter Patch Delivery requires:
1. Special temporary support catheters
2. Specially tailored surgical patches from different materials.

(2) Objects of this Invention

An object of this invention is to safely repair heart defects.

Further objects are to achieve the above with devices that are sturdy, compact, durable, lightweight, simple, safe, efficient, versatile, ecologically compatible, energy conserving, and reliable, yet inexpensive and easy to manufacture, install, operate, and maintain.

Other objects are to achieve the above with a method that is rapid, versatile, ecologically compatible, energy conserving, efficient, and inexpensive.

The specific nature of the invention, as well as other objects, uses, and advantages thereof, will clearly appear from the following description and from the accompanying drawings, the different views of which are not necessarily scale drawings.

CATALOGUE OF ELEMENTS

As an aid to correlating the terms of the claims to the exemplary drawings, the following catalog of elements and steps is provided:

10 Outer Sheath
12 Distal Balloon
13 Supporting Balloon
14 Loading Wire
16 Floppy Disk
18 Inflation Tube, Distal
19 Inflation Tube, Proximal
20 Fabric Patch
22 Hole
24 Square Type Patch
26 Rhomboid Patch
28 Sleeve Patch
30 Purse String
31 Loop
32 Nylon Thread
33 Double Nylon Thread
34 Proximal Balloon

DESCRIPTION OF THE PREFERRED EMBODIMENTS(S)

Figure 1:
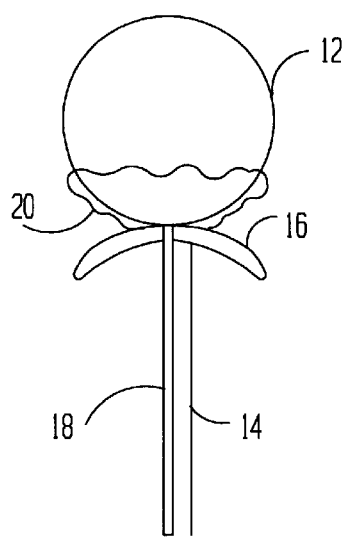
FIG. 1 is a representation of an inflated distal balloon and a floppy disk.

Referring to FIG. 1 there may be seen a representation of an inflated distal balloon 12. Floppy disk 16 in in FIG. 1 is in an expanded position. Loading wire 14 is connected to patch 20.

As used herein the term "loading wire" is used to include a thin metal tube of small diameter with a loop of thread extending through the tube. The distal portion of the loop of thread may extend around an element. The proximal portion of the thread is tied together. In the tied condition the thread may be used to withdraw the looped element. By cutting the thread and pulling on one thread, the loop may be disengaged from the element. Nylon is the preferred material for the thread.

The patch 20 is fabric and placed around the balloon 12. The patch is similar to that shown in FIG. 4 and has hole 22 in the center. The balloon is connected to the inflation tube 18. Which extend through the hole 22 in the patch.

Figure 8:
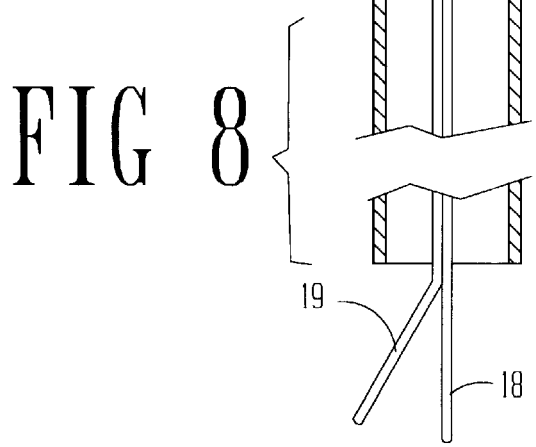
FIG. 8 is a representation of two balloons and a flat patch in a long sheath.

To place the patch in position the balloon, patch, floppy disk, loading wire and inflation tube are all within a long sheath (similar to that shown in FIG. 8). Using well known procedures the long sheath is inserted placing the balloon within the defect within the heart. With the balloon distal of the defect, the sheath will be retracted below the balloon but still holding the floppy disk 16. The balloon 12 will be inflated by forcing the inflation fluid through the inflation tube 18. With the balloon fully inflated the balloon will be moved toward the defect till the balloon is firmly seated upon the defect with the patch 20 in contact with the defect. With the balloon held in this position by the inflation tube the sheath is pulled below the floppy disk 16 which expands to hold the balloon in position on the defect. The sheath is then removed.

The balloon will remain in this position until the patch endothelialize.

After the patch endothelializes, the balloon is deflated by permitting the fluid to flow outward from the inflation tube 18. The balloon then may be pulled from the distal side of the defect and the hole 22 closed as described hereafter. At the same time the floppy disk is withdrawn by the withdrawal of the balloon. If the is patch is safely attached to the septum, the loading wire is withdrawn; otherwise it can still retrieve the patch.

The surgical patches may be made from different materials. It is preferable they are made from thin porous material. Such materials include but not limited to woven materials (i.e. Dacron), to poly-urethane foam to Gor-tex etc. The Transcatheter patches may be tailored to various desired forms according to the economy and shape of the defects.

Two forms may be used. One is the flat patch such as square type 24 shown in FIG. 4 or rhomboid type 26 as shown in FIG. 5. The other type patch is a sleeve patch 28 which will be described later. The flat patches are associated with subsequent overlapping over the defect; they are therefore more appropriate for more irregular defects.

The flat patches are tailored with the central rounded opening or hole 22. The hole is connected through a purse string 30 to a loading wire 32. (The tube is not shown in FIGS. 4 & 5).

Figure 4:
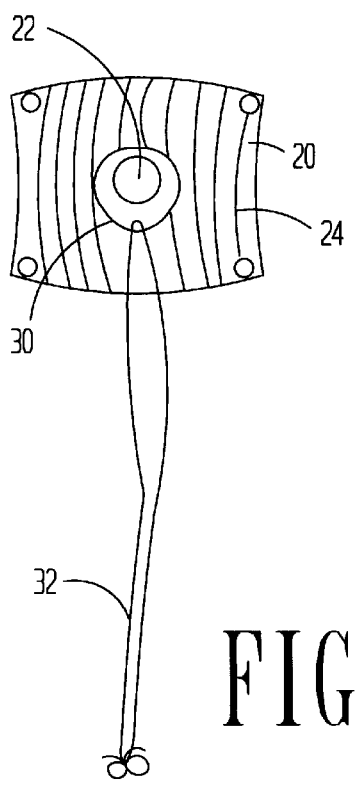
FIG. 4 is a representation of a square flat patch.
Figure 5:
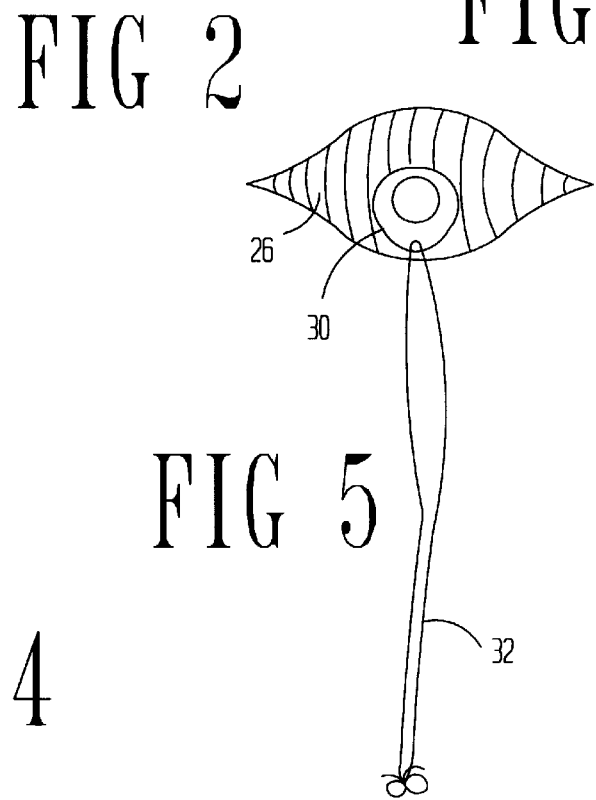
FIG. 5 is a representation of a rhomboid flat patch.

Referring to FIG. 4 is shown a square type 24 of the patch 20.

The rhomboid shape patch 26 as seen in FIG. 5 also has a two millimeter hole opening in the center of the patch. The edge of the holes are reinforced by suturing. A double nylon thread is passed through both edges of the hole for possible retrieval purposes also as the purse string 30 effect. Like the square patch, is the rhomboid patch 26 is not attached to the floppy disk 16 nor to a proximal balloon.

It is necessary to determine the endothelialize time of the porous patch material. It is after the patch has endothelialized that the distal balloon will be deflated and removed. When polyurethane foam is the fabric, 48 hours of support is required by the distal balloon 12.

Figure 2:
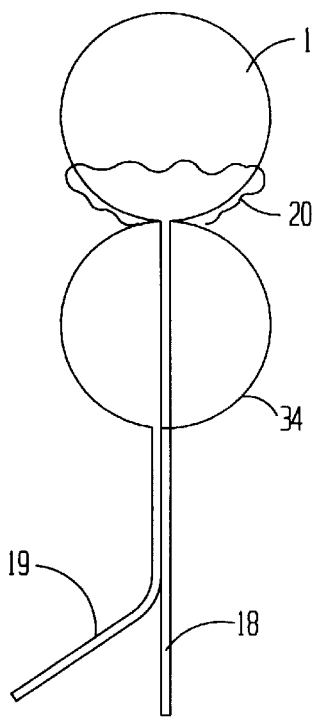
FIG. 2 is a representation of an inflated distal balloon and proximal balloon.

Referring to FIG. 2 there may be seen a different method of the temporary anchoring of the patch 20 to the defect. The double balloon method will have the same distal balloon 12 with the patch 20 attached there to. However proximal balloon 34 will be used to form the same function as the floppy disk 16 preformed in the embodiment of FIG. 1. The double balloon with a patch is introduced into the long sheath 10 as shown in FIG. 8. The long sheath is positioned into the heart defect on the distal side of the defect of the cardiac chamber. The long sheath is pulled back from the distal balloon 12. The distal balloon is inflated through the tube 18, expanding the patch 20 and is pulled back until occluding the defect. The long sheath 10 is withdrawn. The proximal balloon is inflated by inflation tube 19 supporting the patch from the proximal septal side.

The proximal balloon 34 may have a lumen extending through it. Otherwise the inflation tube 18 and loading wire (not shown in FIG. 8) extends along the outside of the proximal balloon 34.

Figure 3:
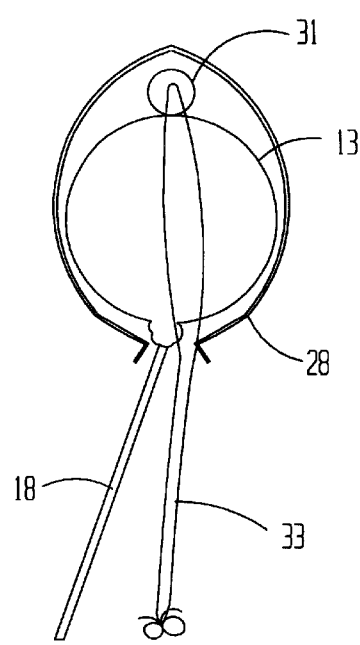
FIG. 3 is a representation of an inflated balloon in a sleeve patch.

Referring to FIG. 3 there may be seen a sleeve patch 28. Supporting balloon 13, inflated by inflation tube 18, takes the precise shape of the sleeve patch 28. The sleeve patches are more appropriate for rounded defects. Balloon 13, like balloon 34 may have a lumen.

The material of the patch 28 which is in the form of a sleeve which will fit precisely over the distal balloon. A small nylon loop 31 is sutured at the internal apical surface of the sleeve 28. A double nylon thread 33 of a loading wire (not shown) is pierced through the loop 31 for purposes of retrieval.

Figure 6:
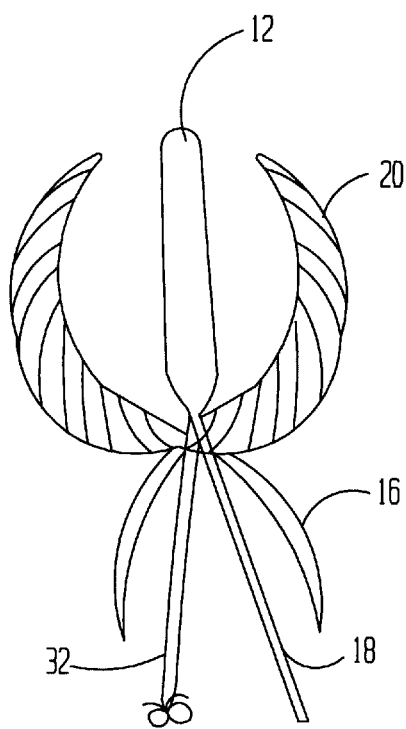
FIG. 6 is a representation of an assembly of balloon, flat patch, floppy disk and inflation tube.

FIG. 6 is a depiction of a flat patch (like the patch 24) mounted around a balloon (like balloon 12) before the combination is placed into a insertion sheath to be inserted in place.

Figure 7:
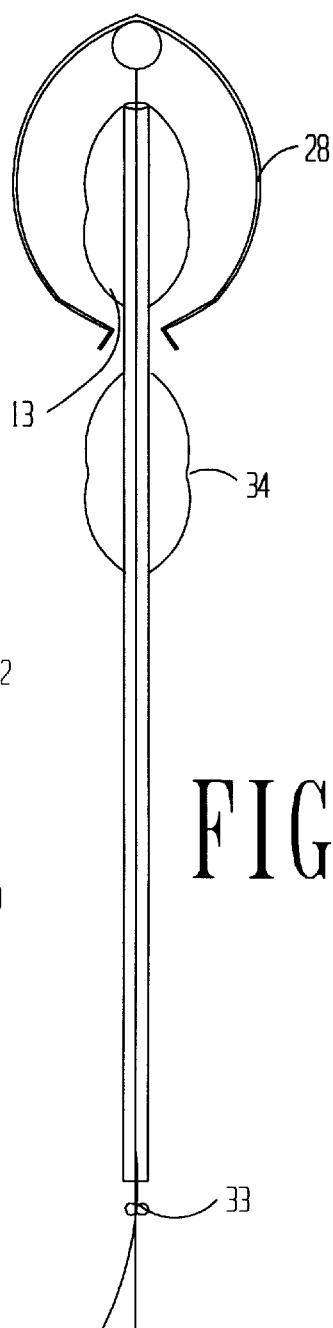
FIG. 7 is a representation of a sleeve patch and two balloons.

FIG. 7 is a depiction of a sleeve patch (like patch 28) as it would be placed around the distal balloon (like 13) and proximal balloon (like 24) before the balloons were inflated. The parts are shown before the equipment would be placed within an insertion sheath.

Either the flat patch or the sleeve patch may be made radio-opaque using commercially available radio-opaque threads.

The embodiments shown and described above are only exemplary. I do not claim to have invented all the parts, elements or steps described. Various modifications can be made in the construction, material, arrangement, and operation, and still be within the scope of my invention.

The restrictive description and drawings of the specific examples above do not point out what an infringement of this patent would be, but are to point out the advantages and the progressive contribution to the useful arts and to enable one skilled in the art to make and use the invention. The limits of the invention and the bounds of the patent protection are measured by and defined in the following claims.

I claim as my invention:

1. The method of placing a patch on a heart defect comprising the steps of:
    a) preparing a patch of a flexible endothelializable material,
    b) placing the prepared patch on the proximal side of an uninflated distal balloon,
    c) placing the patch and the balloon distally of the defective opening,
    d) inflating the balloon,
    e) moving the balloon and the patch on the balloon firmly against the defective opening,
    f) permitting the patch to endothelialize, then
    g) deflating and removing the balloon.

2. The method as defined in claim 1 further comprising:
    after moving the patch firmly against the defective opening, then
        h) inflating a proximal balloon connected to the distal balloon proximally of the defective opening.

3. The method as defined in claim 1 further comprising:
    after moving the patch against the defective opening, then
        h) placing a floppy disk proximally of the defective opening.

4. A device for closing a defective opening in a heart comprising:
    a) a long sheath having a distal end and a proximal end,
    b) a distal uninflated balloon in the long sheath adjacent the distal end, c) a destal inflation tube extending in the sheath from the distal balloon to and beyond the proximal end,
d) a housing device proximal of the balloon in the sheath,
   dd) a patch of flexible endothelializable material between the balloon and the holding device, and
e) said holding device attached to the distal inflation ever close to the distal balloon.

5. The device as defined in claim 4 further comprising: said holding device is in the form of
   f) a proximal uninflated balloon with,
   g) a proximal inflation tube extending in the sheath from the proximal balloon to beyond the proximal end of the sheath.

6. The method of occluding a heart defect comprising the steps of:
   a) placing a distal balloon on a distal side of the defective opening,
      aa) placing a patch of a flexible endothelializable material between the distal balloon and the defective opening,
   b) placing a proximal balloon which is connected to the distal balloon on a proximal side of the opening,
   c) inflating both balloons, and
   d) removing the ballons after the patch endothelializes.

\* \* \* \* \*